United States Patent [19]

Tanaka et al.

[11] Patent Number: 4,950,600
[45] Date of Patent: Aug. 21, 1990

[54] METHOD OF IMMOBILIZING ENZYMES OR MICROBES WITH ALGINATE HAVING A LOW MANNURONIC ACID TO GULURONIC ACID RATIO

[75] Inventors: Hideo Tanaka, Ibaraki; Shinzi Irie, Chiba, both of Japan

[73] Assignees: Kabushiki Kaisha Kibun; Kabushiki Kaisha Kibun Fudokenifa, both of Tokyo, Japan

[21] Appl. No.: 143,525

[22] Filed: Jan. 13, 1988

[30] Foreign Application Priority Data

Jan. 16, 1987 [JP] Japan .................................. 62-5887

[51] Int. Cl.$^5$ ........................ C12N 11/10; C12N 11/04
[52] U.S. Cl. ...................................... 435/178; 435/182
[58] Field of Search ............... 435/174, 177, 178, 182; 530/813; 536/3

[56] References Cited

U.S. PATENT DOCUMENTS

| | | | |
|---|---|---|---|
| 4,391,909 | 7/1983 | Lim | 435/178 |
| 4,407,957 | 10/1983 | Lim | 435/178 |
| 4,603,854 | 7/1986 | Schmidt et al. | 426/574 |
| 4,663,287 | 5/1987 | Barker | 435/188 |

FOREIGN PATENT DOCUMENTS

0028900A1  5/1981  European Pat. Off. .
0065476A1 11/1982  European Pat. Off. .

OTHER PUBLICATIONS

DE-Buch: Rehm, H. J., Reed, G.: Biotechnology, vol. 7a, Weinheim: VCH-Verlagsgesellschaft mbH, 1987.
F. Paul et al, "Enzyme Microb. Technol.", (1980), vol. 2, pp. 281–287.
A. L. Dainty et al, "Biotechnology and Bioengineering", (1986), vol. 28, pp. 210–216.
Biotechnology and Bioengineering, vol. 24, No. 7, 1982, pp. 1507–1517, M. Kierstan et al., "Studies on the Characteristics of Alginate . . . ".
Chemical Abstracts, vol. 83, No. 26, Dec. 29, 1975, pp. 97–98, Abstract No. 207815d, Seeley et al., "Binding of Alkaline Earth . . . ".

*Primary Examiner*—David M. Naff
*Attorney, Agent, or Firm*—Nixon & Vanderhye

[57] ABSTRACT

Enzymes or microbes are immobilized by using low mannuronic acid to guluronic acid (M/G) ratio alginate to produce an alginate gel having improved strength. An aqueous solution containing an enzyme or microbe and alginate having an M/G ratio of 0.01–0.8 (preferably 0.01–0.3) is contacted with an aqueous solution of barium ion or strontium ion to gel the alginate.

7 Claims, 2 Drawing Sheets

METHOD OF IMMOBILIZING ENZYMES OR MICROBES WITH ALGINATE HAVING A LOW MANNURONIC ACID TO GULURONIC ACID RATIO

The present invention relates to a method of preparing an immobilized enzyme or an immobilized microbe, wherein an enzyme or a microbe is immobilized by the use of sodium alginate and barium ion or strontium ion.

Immobilized enzymes and microbes have been developed for the purpose of enabling continuous and recycled use of enzymes or microbes, the latter being processed and entrapped in a certain space for continuous reaction and recycled use.

Methods that have been proposed for preparation of immobilized enzymes or microbes include the substrate-binding method, the cross-linking polymerization method, the gel-inclusion method, etc.

Of these, the gel-inclusion method immobilizes enzymes and microbes by enclosing them with a gel or polymer matrix; and a method using sodium alginate has already been known in which, in general, calcium ion is used as a gelling agent.

However, the gel-inclusion immobilization method of the prior art using sodium alginate and calcium ion has involved certain disadvantages in that the strength of the gel composed of alginate salts decreases remarkably under the influence of various salts contained in the reaction liquid or a change in pH, and in that the gel is dissolved by the presence of chelating agents such as phosphate ion, etc.

Attempts have therefore been made to add large amounts of calcium ion, a gelling agent, to the reaction liquid for the purpose of increasing the gel strength. However, although the addition of a large amount of calcium ion improves the gel strength, it results in other troubles; it not only brings about undesirable effects on the isolation and purification of the reaction products, but also inhibition of the activity of enzymes such as glucose isomerase, etc. or the microbes producing such enzymes, e.g., Streptomyces phaeochromogenes, Bacillus Coagulans, etc.

The present inventors actively investigated possible solutions for the aforementioned problems and thereby obtained the following findings: the composition ratio between the constituents of alginic acid, i.e., the D-mannuronic acid (M) to L-guluronic acid (G) residue ratio (M/G ratio), is critical to the gel strength. More specifically, what is important is not only the simple M/G ratio but also the composition ratios between (1) a part consisting of M residues only, (2) a part consisting of G residues only, and (3) a part consisting of both M and G residues. The main function of the G block is to bind with a metal ion of a gelling agent to form a firm gel. Furthermore, a firmer and more stable binding is made between the G block and the metal ion of a gelling agent when the metal ion used is barium ion or strontium ion, rather than when calcium ion is used as in the prior art. Based on these findings, the present inventors have completed the present invention.

In other words, the present invention provides a method for preparation of an immobilized enzyme or an immobilized microbe characterized in that after an enzyme or a microbe is added to an aqueous solution of sodium alginate having the M/G ratio of 0.01–0.8, the mixed solution is brought into contact with an aqueous solution containing barium ion or strontium ion for gelation.

Figure 1:
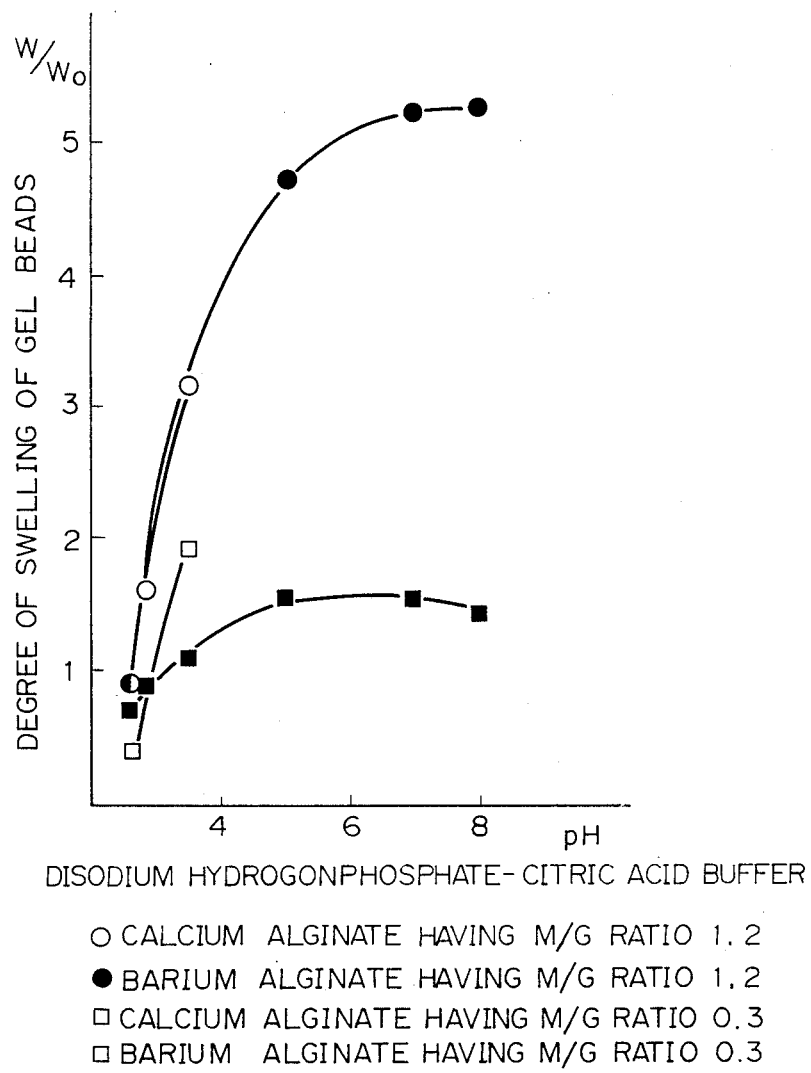
FIG. 1 shows the degree of swelling of barium alginate gel beads and calcium alginate gel beads in a phosphate buffer at various pH.

The sodium alginate used in the present invention can be selected from a marketed sodium alginate prepared by extracting alginic acid from brown algae in a chemical process and turning it into a sodium salt. It is necessary to select one with an M/G ratio of 0.01–0.8, i.e. the ratio of the residues of D-mannuronic acid (M) to L-guluronic acid (G) which constitute the alginic acid. More preferably the M/G ratio is 0.01–0.2.

Sodium alginate with such a low M/G ratio can be selected from the marketed ones described above, but can also be prepared specially by such methods as selecting a type of seaweed with a high G content, certain parts of a seaweed (e.g., the stem part) with a high G content, or the season (May to August) in which the seaweed is gathered for extraction, or blending sodium alginate with a high G content.

Sodium alginate having a G content in the range specified above can provide a gel with greater strength which is stable and resistant to the effects of heat and/or chelating agents, the effects of electrolytes, or changes in pH.

The present inventors also found that, after investigating the M/G ratio in more detail, a part generally classified as G can be divided into two blocks, one consisting of G only and the other consisting of both M and G; of these two blocks, the G block plays a role in forming a firm gel by binding with barium ion or strontium ion.

The aforementioned idea of using sodium alginate having a high G content, that is, a relatively small M/G ratio, and of using barium ion or strontium ion was conceived on the basis of these findings.

The concentration of sodium alginate in the solution to which an enzyme or a microbe has been added is preferably 0.5 (W/V)%–8 (W/V)%, more preferably 3 (W/V)%–6 (W/V)%.

There is no restriction on the types of enzymes or microbes that can be used in the present invention; examples of enzymes include oxido-reductases such as alcohol dehydrogenase, D-amino acid oxidase, catalase, etc., transferases such as transketolase, adenylate kinase, hexokinase, etc., hydrolases such as $\beta$-galactosidase, penicillinase, lipase, esterase, etc., lyases such as fumarase, aspartase, threonine aldolase, $\beta$-tyrosinase, etc., isomerases such as glucose isomerase, alanine isomerase, etc., and ligases such as glutathione synthetase, glutamine synthetase, etc.

There is no particular restriction on the types of microbes that can be used in the present invention as long as they are included in the group consisting of bacteria, yeast, fungi, and actinomycetes, etc. having an enzymatic activity. Cell organelles, cell fractions, and processed products of enzymes or microbes having enzymatic activity can also be used.

When an enzyme is immobilized, the preferable concentration of the enzyme is 0.01 (W/V)%–20 (W/V)%, and when a microbe is immobilized, the preferable concentration of the microbe is 0.01 (wet weight/V)%–50 (wet weight/V)%. When a live bacterial body is immobilized, the range of concentration of the microbe at the time of immobilization can be selected from a wider range because the number of live bacteria in the gel can be increased by culturing the immobilized microbe in a suitable culture medium.

An aqueous solution containing barium ion used for gelation is prepared by dissolving a barium salt in water. Specific examples of barium salts include barium chloride, barium nitrate, barium acetate, etc., and of these, barium chloride is suitable because of its low price.

Likewise, examples of strontium salts include strontium chloride, strontium nitrate, strontium acetate, etc., and strontium chloride is particularly suitable because of its low price.

The concentration of barium ion or strontium ion used in the present invention is 0.01M–1.0M, preferably 0.02M–0.5M.

The method of gel preparation can be determined by a method selected from the following (1)–(3) depending on the purpose for which the immobilized enzyme or immobilized microbe will be utilized.

(1) By adding a mixed solution of sodium alginate and an enzyme or a microbe (hereinafter referred to as said mixed solution) dropwise from the nozzle of a syringe, a pipette, etc. into an aqueous solution containing barium ion or strontium ion, an immobilized product may be obtained in the form of a bead.

(2) By forcing out said mixed solution from the nozzle of a syringe, a pipette, etc., continuously into an aqueous solution containing barium ion or strontium ion, an immobilized product may be obtained in the form of a fiber.

(3) By bringing said mixed solution into contact with barium ion or strontium ion in an aqueous solution after said mixed solution has been case on a flat plate or impregnated in filter paper or gauze, an immobilized product may be obtained in the form of a membrane.

In each of the methods described above, such conditions as the duration of the contact with barium ion or strontium ion, pH, temperature, etc. should be selected from within a suitable range of conditions which do not adversely affect the activity of the enzyme or the microbe; normally, the duration of the contact of said mixed solution with an aqueous solution containing barium ion or strontium ion is selected from the range 0.5–24 hours, the pH from the range 3–11, and the temperature from the range 4°–50° C.

In the following, the stability of the gel obtained by the present invention is examined by way of tests concerning the degree of swelling of the gel.

Tests

1. Stability of a gel in phosphate solution (degree of swelling)

Into 10 ml of 0.1M $KH_2PO_4$ aqueous solution were placed 6 gel beads ($\phi$=3 mm) prepared by adding 1.5% sodium alginate aqueous solution dropwise into 0.3 M barium chloride aqueous solution. The solution was kept at 30° C. for 24 hours and then the degree of swelling of the gel beads (weight of gel beads/initial weight of gel beads) was determined.

The results are shown in Table 1.

TABLE 1

|  | Test results | Control results |
|---|---|---|
| M/G ratio | 0.3 | 1.2 |
| Degree of swelling | 1.3 | 3.4 (partially dissolved) |

2. Stability of gel in alkaline solution (degree of swelling)

Into 10 ml samples of phosphate buffer solution and acetic acid - barbital buffer solution were place 6 gel beads each of barium alginate ($\phi$—3 mm) prepared by a method similar to that described above. The solution was dept at 30° C. for 74 hours and then the degree of swelling of the gel beads (weight of gel beads/initial weight of gel beads) was determined. The results are shown in FIG. 1 and FIG. 2 together with those for calcium alginate of the prior art.

Figure 2:
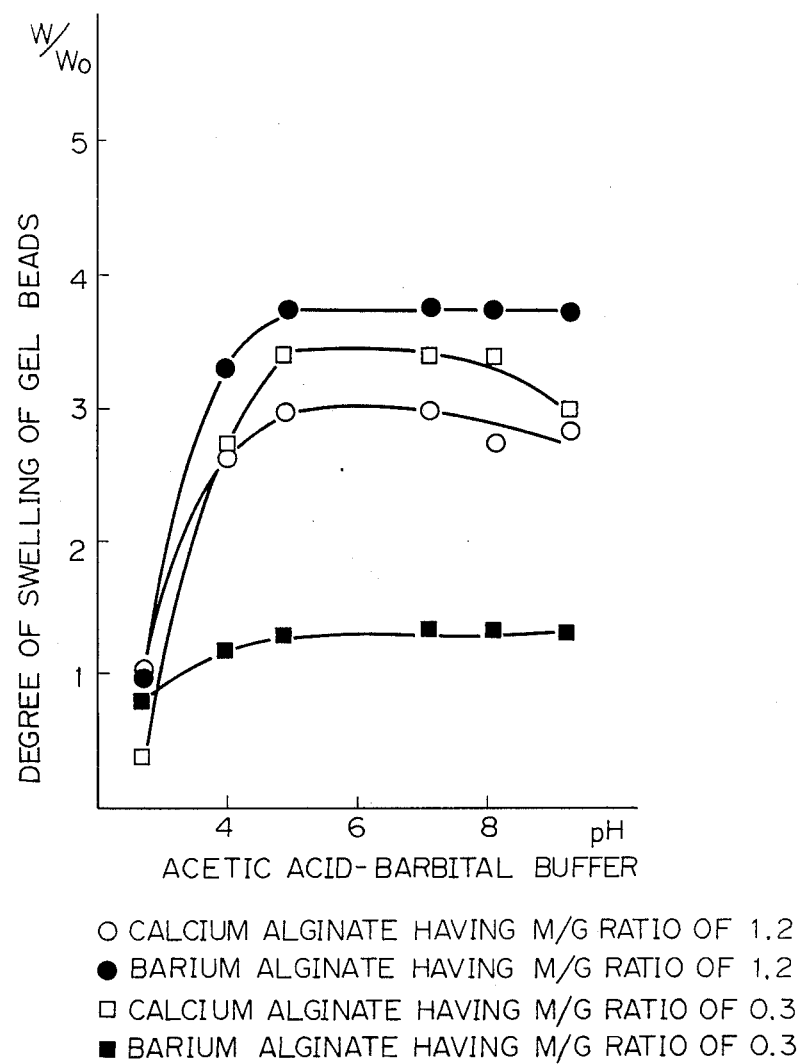
FIG. 2 shows the degree of swelling of barium alginate beads and calcium alginate beads in an acetic acid-barbital buffer solution at various pH.

As is clear from FIG. 1, in a phosphate buffer solution, calcium alginate gel beads with an M/G ratio of 1.2 and 0.3 were both dissolved at a pH not lower than 3, and barium alginate gel beads of the present invention with an M/G ratio of 0.3 showed a swelling degree of only about 1.5. However, with barium alginate beads having an MG ratio of 1.2, i.e. outside the M/G ratio range of the present invention, the degree of swelling became as much as 5. On the other hand, in an acetic acid - barbital buffer solution, barium alginate gel beads of the present invention having an M/G ratio of 0.3 showed a degree of swelling of less than 1.5 even at a pH no lower than 4, while barium alginate gel beads having an M/G ratio of 1.2, and calcium gel beads having an M/G ratio of 0.3 and 1.2 showed respective degrees of swelling twice as large.

EXAMPLE

The present invention is specifically illustrated by the following examples, but these are in no way to be taken as limiting.

The strength of gel beads referred to in the following examples and controls was expressed by the load per unit cross section in consideration of bead diameter, and was obtained by the equation given below.
Equation:

$$\frac{\text{load required to break the beads (g)}}{(\text{beads diameter} \times 0.5)^2 \times 3.14} = g/cm^2$$

Example 1, Control 1

1.0 g of sodium alginate having an M/G ratio of 0.3 was dissolved in 25 ml of water. To this solution, 6 g of glucose isomerase-containing frozen bacterial body obtained by culturing Streptomyces Phaeochromogenes (manufactured by Godo Shusei; activity: 550 unit/g of frozen bacterial body) was added to prepare a mixed solution. The mixed solution was added dropwise to 0.3 M barium chloride aqueous solution through a nozzle 1 mm in internal diameter to prepare gel beads. After that, stirring was continued at 25° C. for 2 hours to complete gelation. Filtering and washing with water was repeated to obtain 30 ml of immobilized actinomycetes.

The activity of glucose isomerase of the immobilized actinomycetes was determined by the amount of fructose produced at 70° C. in a 0.1 M phosphate buffer solution of pH 7.0 using glucose given in the form of a 0.1M solution as a substrate. The results showed an activity of 62.7 (unit/ml-immobilized actinomycetes). The activity yield was 57.0%.

By way of comparison, sodium alginate having an M/G ratio of 1.2 was used to obtain immobilized actinomycetes by procedure similar to that described above.

The activity was 62.7 unit/ml. The activity yield was 57.0%.

The strength of the immobilized actinomycetes gel beads thus obtained is shown in Table 2.

TABLE 2

|  | Example 1 | Control 1 |
|---|---|---|
| M/G ratio | 0.3 | 1.2 |
| Strength of gel beads | 1.75 kg/cm$^2$ | 1.57 kg/cm$^2$ |

Example 2, Control 2

1.0 g of sodium alginate having an M/G ratio of 0.3 was dissolved in 25 ml of water. To this solution, 0.25 g of partially purified and diluted β-galactosidase powder (manufactured by ICN Nutritional Biochemical, activity at 25° C. and pH 7.5:80000 unit/g) was added to prepare a mixed solution. This solution was added dropwise into a 0.3M strontium chloride aqueous solution through a nozzle 1 mm in internal diameter to prepare gel beads. Stirring was continued at 25° C. for 2 hours to complete gelation. After that, filtering and washing was repeated to obtain 30 ml of immobilized β-galactosidase.

The activity of the immobilized β-galactosidase was determined by the amount of glucose produced at pH 7.5 and 25° C. using lactose given in the form of 9% (W/V) solution as substrate; the results showed the activity of 520 (unit/ml-immobilized β-galactosidase).

The activity yield was obtained by the equation given below.

$$AY = \frac{(A \text{ of immobil. } \beta - \text{gal.}) \times (Y \text{ of immobil. } \beta - \text{gal.})}{(A \text{ of used } \beta - \text{gal.}) \times (Y \text{ of used } \beta - \text{gal.})} \times 100$$

By way of comparison, sodium alginate having an M/G ratio of 1.2 was used to obtain immobilized β-galactosidase by a procedure similar to that described above. The activity was 520 (unit/ml-immobilized β-galactosidase), and the activity yield was 65%.

The strength of the immobilized β-galactosidase gel beads thus obtained is shown in Table 3.

TABLE 3

|  | Example 2 | Control 2 |
|---|---|---|
| M/G ratio | 0.3 | 1.2 |
| Strength of gel beads | 700 g/cm$^2$ | 63 g/cm$^2$ |

The gel of immobilized enzymes or immobilized microbes obtained by the preparation methods of the present invention have a remarkably superior strength to those prepared by the gel-inclusion methods of the prior arts using sodium alginate and calcium ion, and are stable even when exposed to changes in pH or the presence of chelating agents, as well as allowing ling-term operation without such troubles as plugging, etc., when charged in a column for a continuous flow reaction.

Furthermore, the immobilization method of the present invention has the advantage that it allows immobilization in one step without requiring complex processes.

What is claimed is:

1. A method of preparing an immobilized enzyme or an immobilized microbe comprising the steps of adding an enzyme or a microbe to an aqueous solution of sodium alginate containing D-mannuronic acid residues and L-guluronic acid residues in a ratio of D-mannuronic acid residue to L-guluronic acid residue of 0.01–0.3, and thereafter contacting the solution with an aqueous solution containing barium ion or strontium ion whereby said sodium alginate is gelled by said barium ion or strontium ion and said enzyme or microbe is immobilized.

2. A method according to claim 1 in which the ratio is 0.01–0.2.

3. A method according to claim 1 in which the concentration of sodium alginate in aqueous solution is 0.5–8 (W/V)%.

4. A method according to claim 3 in which the concentration of sodium alginate is 3–6 (W/V)%.

5. A method according to claim 1 in which the concentration of the enzyme or a microbe in the aqueous solution of sodium alginate is 0.01–20 (W/V)% or 0.01–50 (W/V)%, respectively.

6. A method according to claim 1 in which the aqueous solution containing barium ion or strontium ion is an aqueous solution of a soluble barium salt or a soluble strontium salt.

7. A method according to claim 1 in which the aqueous sodium alginate solution containing an enzyme or a microbe is contacted with the aqueous solution containing barium ion or strontium ion for 0.5–24 hours at a pH of 3–11 and a temperature of 4°–50° C.

* * * * *

UNITED STATES PATENT AND TRADEMARK OFFICE
CERTIFICATE OF CORRECTION

PATENT NO. : 4,950,600

DATED : August 21, 1990

INVENTOR(S) : Tanaka et al

It is certified that error appears in the above-identified patent and that said Letters Patent is hereby corrected as shown below:

ON TITLE PAGE: Item [73]

[73] Assignees:, please correct the spelling of the second assignee to read: --Kabushiki Kaisha Kibun Fudokemifa--

Signed and Sealed this

Twenty-fifth Day of February, 1992

*Attest:*

HARRY F. MANBECK, JR.

*Attesting Officer*     *Commissioner of Patents and Trademarks*